United States Patent [19]
Bradley et al.

[11] 3,936,374
[45] Feb. 3, 1976

[54] VARIABLE JET SEPARATOR

[75] Inventors: M. P. Timothy Bradley, Shaker Heights; Jacob Shen, Akron, both of Ohio

[73] Assignee: The Standard Oil Company, Cleveland, Ohio

[22] Filed: Sept. 30, 1974

[21] Appl. No.: 510,609

[52] U.S. Cl.................. 210/31 C; 55/17; 55/67; 55/197; 210/198 C
[51] Int. Cl.².............................. G01D 15/08
[58] Field of Search ........ 55/17, 67, 197; 210/31 C, 210/198 C

[56] References Cited
UNITED STATES PATENTS

| | | |
|---|---|---|
| 485,915 | 11/1892 | Duckham.............................. 55/17 |
| 2,607,439 | 8/1952 | Dickens et al.......................... 55/17 |
| 3,279,155 | 10/1966 | Lambert .............................. 55/17 X |
| 3,859,205 | 1/1975 | Rega et al............................. 55/17 X |

Primary Examiner—John Adee
Attorney, Agent, or Firm—John F. Jones; Sherman J. Kemmer

[57] ABSTRACT

A variable jet separator apparatus is described which is useful for separating mixtures of gases and mixtures of liquid having different molecular-weight components in them.

5 Claims, 4 Drawing Figures

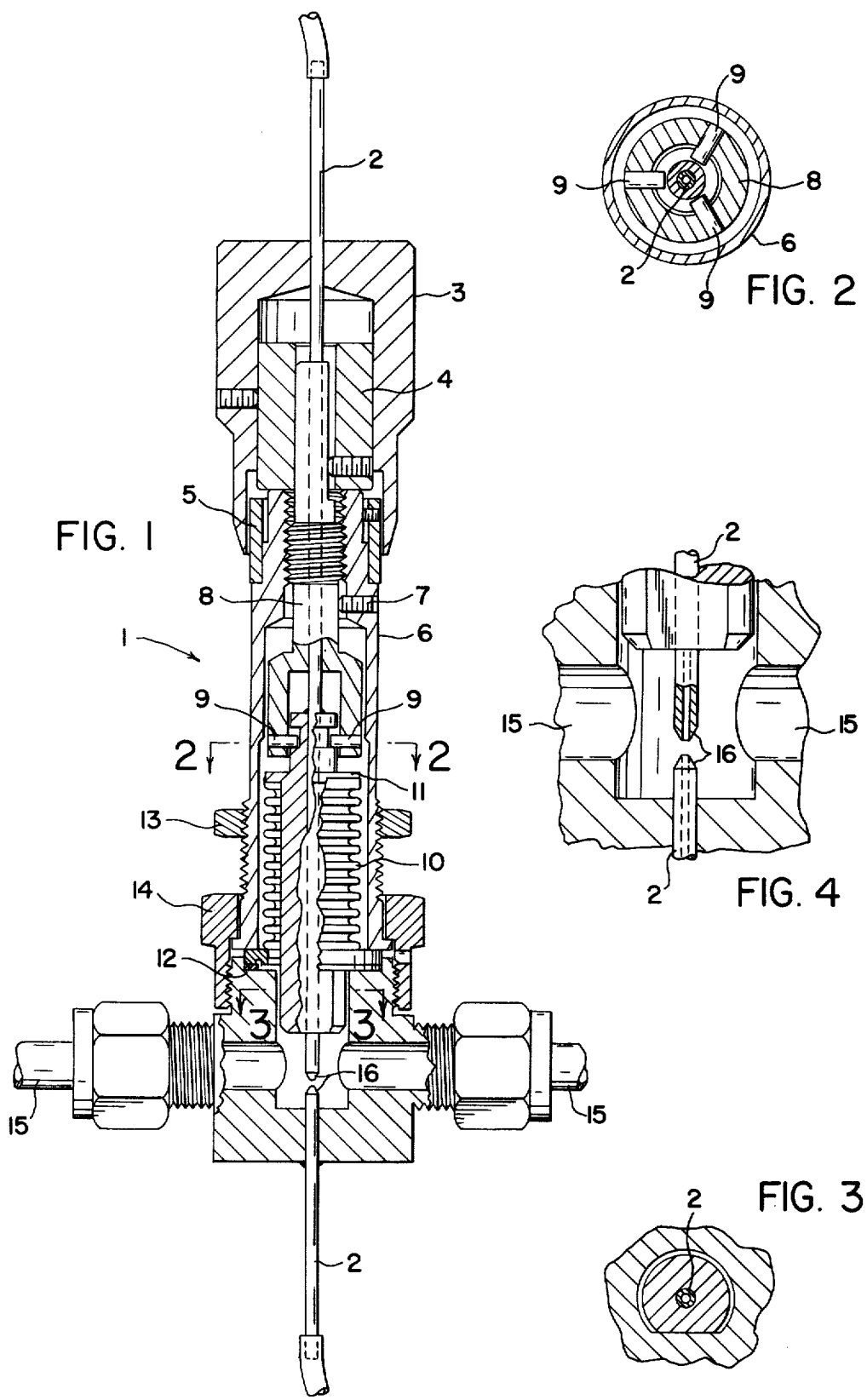

VARIABLE JET SEPARATOR

The present invention relates to a variable jet separator and more particularly pertains to a valve which is a variable jet separator capable of operating over a wide range of conditions.

The variable jet separator of this invention is particularly useful in gas chromatograph-mass spectrometer interfacing and is tunable to separate different molecular-weight compounds as well as other uses which will be disclosed hereinafter.

This invention can be illustrated by reference to the accompanying drawings wherein:

FIG. 1 is a side elevation view partly in section showing an embodiment of the variable jet separator of the present invention.

FIG. 2 is a view taken along line 2—2 in FIG. 1.

FIG. 3 is a view taken along line 3—3 in FIG. 1.

FIG. 4 is a close-up fragmented view of the variable capillary jet arrangement of FIG. 1.

The variable jet separator apparatus 1 is made up of two capillary tubes 2. The upper tube 2 can be a conduit for the effluent from a gas chromatograph into the separator and the lower tube 2 can be a conduit leading into a mass spectrograph. The upper tube is slidably mounted in a metering handle 3 which surrounds a bushing 4 and rides on the barrel 5 which surrounds the bonnet 6. The adjustability of the metering handle can be controlled by a locking screw 7 which can be made to contact and restrict movement of the actuator 8. The upper capillary tube 2 is centered within the apparatus by pins 9 and extends downward through a flexible bellows 10 which is confined between a stem 11 and a gasket 12. The variable jet separator apparatus 1 may be mounted onto a stand, panel, etc., by means of a jam nut 13 and bonnet nut 14. Two outlets 15 to vacuum pump and the like are provided near the bottom of the apparatus. The capillary tubes 2 are provided with tapered ends 16 and the tapered ends of the upper and lower capillary tubes 2 are separated in a chamber within the apparatus. The distance between the tapered ends 16 is controlled by raising or lowering the upper capillary tube 2 by turning the metering handle 3. Thus, the apparatus is tunable by adjustment of the distance between the tapered ends 16 to satisfy any particular situation, and the distance depends on which two liquids or gases are being passed through the apparatus.

The apparatus of this invention is universal in its application in that it can be used as a gas or liquid enrichment separator and a splitter and is particularly useful as a tunable mass spectrometer interface for coupling the effluent line of a gas or liquid chromatograph to a mass spectrometer. The wide range of movement of the relative positions of the jet nozzles from each other and the ease of setability allow great operating flexibility.

In a specific example of the use of the apparatus of this invention, the upper capillary tube can be connected to a gas chromatograph column and transfer line and the lower capillary tube is connected to a mass spectrograph analyzer. The two outlets or side parts on the apparatus are connected to a vacuum pump which creates a partial vacuum on the internal valve system. The spacing between the jets can be closely adjusted as desired by turning the metering handle in a clockwise or counterclockwise direction. During its operation, the apparatus of this invention can be heated or cooled by conventional means such as a heating or cooling jacket and the like.

The effluent from the gas chromatograph, which contains the separated chemical component and the carrier gas (helium), passes through the variable jet separator through the upper capillary tube and comes out the jet of this tube, at which point the helium diffuses faster and is selectively pulled off through the two outlets while the enriched chemical component, which always is of higher molecular weight than helium, passes into the jet of the lower capillary tube and on into the mass spectrometer.

The apparatus of the present invention has many advantages including high performance over a wide range of operating conditions, it is not limited in terms of the carrier fluid flow, it is readily tunable to separate different molecular-weight compounds, it can be adjusted "on the fly" to enhance trace component sensitivity when used in conjunction with a mass spectrometer, it can be used for liquid chromatography-mass spectrometer interface particularly when the solute has a higher molecular weight than the solvent, it can produce variable yields from 100 to 0, and it can be used as an enrichment sampler for air or liquid pollution studies.

We claim:

1. A variable jet separator apparatus useful in chromatograph-mass spectrometer interfacing for coupling the effluent line of a gas or liquid chromatograph to a mass spectrometer comprising an upper capillary tube and a lower capillary tube, both of said tubes having tapered ends, the ends of said tubes being located adjacent to one another in an enclosed chamber, one of said tubes being adjustable to move towards or away from said other tube, one of said tubes being coupled to the effluent line of a gas or liquid chromatograph and the other of said tubes being coupled to a mass spectrometer.

2. The apparatus of claim 1 wherein the upper tube is adjustable and the lower tube is fixed.

3. The apparatus of claim 2 having means for evacuating said chamber at two sides thereof.

4. A process for enriching one liquid or gaseous component in a mixture of a liquid in a liquid or a gas in a gas which is the effluent from a liquid or a gas chromatograph comprising passing said mixture through an upper first capillary tube out the tapered end of said capillary tube across an adjustably controlled gap in an evacuated chamber and into the tapered end of a second capillary tube located adjacent to the tapered end of said first tube, said second tube being coupled to a mass spectrometer.

5. The process of claim 4 wherein the gap may be adjustably controlled during the operation of the process.

* * * * *